United States Patent [19]

Cavitt

[11] 4,229,321
[45] Oct. 21, 1980

[54] PROCESS FOR MAKING A SILVER CATALYST

[75] Inventor: Stanley B. Cavitt, Austin, Tex.

[73] Assignee: Texaco Development Corp., White Plains, N.Y.

[21] Appl. No.: 15,510

[22] Filed: Feb. 26, 1979

[51] Int. Cl.$^2$ ............................................. B01J 23/50
[52] U.S. Cl. .............................. 252/476; 260/348.34
[58] Field of Search ............................... 252/463, 476

[56] References Cited

U.S. PATENT DOCUMENTS

| | | | |
|---|---|---|---|
| 3,033,903 | 7/1977 | Maxwell | 252/476 |
| 3,962,136 | 6/1976 | Nielsen et al. | 252/476 X |
| 4,007,135 | 2/1977 | Hayden et al. | 252/475 X |
| 4,066,575 | 1/1978 | Winnick | 252/475 |
| 4,097,414 | 6/1978 | Cavitt | 252/463 X |

*Primary Examiner*—W. J. Shine
*Attorney, Agent, or Firm*—Carl G. Ries; Robert A. Kulason; Walter D. Hunter

[57] ABSTRACT

A highly-active catalyst is prepared by abrading or wearing away the surface of a silver catalyst whereby 1 to about 10 weight percent of the catalyst is removed. The initial silver catalyst is formed, for example, by impregnating a porous catalyst support with a solution of a silver salt an organic amine solubilizing/reducing agent, an aqueous solvent and a cesium or rubidium salt sufficient to deposit on the support an effective amount of the said alkali metal and subsequently heating the impregnated support at an elevated temperature to evaporate volatiles and activate the catalyst.

26 Claims, No Drawings

PROCESS FOR MAKING A SILVER CATALYST

BACKGROUND OF THE INVENTION

1. Field of the Invention

The instant invention relates to a highly-active silver catalyst useful in the epoxidation of ethylene to ethylene oxide and more particularly to a highly-active silver catalyst prepared by abrading the surface of a previously-prepared, promoted silver catalyst whereby about 1 to about 10 percent by weight of the catalyst is removed.

2. Description of the Prior Art

Supported silver catalysts have long been used for the air oxidation of ethylene and more recently in a so-called "oxygen process". Although the first reference to the use of silver as such a catalyst was made by Walter in British Pat. No. 21,941 (1905), it was not until some thirty years later that the first disclosures were made of the use of silver as a catalyst in the vapor phase oxidation of ethylene to ethylene oxide. See Societe Francaise De Lefort, U.S. Pat. No. 1,998,878 (1935).

A variety of techniques have been developed for the depositing of relatively small, but highly active amounts of silver on surfaces of non-silver support such as alumina. For example, McKim and Cambron in *Canadian Journal of Research*, Volume 27, Section B (1949) at 813–827, describe a method for depositing particulate silver on a support by decomposing silver oxalate in aqueous ethanolamine at 60° C. and forming a paste which is applied to the surface of the support. In U.S. Pat. No. 3,043,854 issued July 10, 1962, to Endler, a silver coating formed by decomposition of a silver carbonate slurry is applied to a catalyst support surface.

It has been disclosed that supported silver catalysts can be prepared by impregnating a porous substrate with certain silver containing solutions and evaporating or decomposing the solutions to deposit silver on the substrate. U.S. Pat. No. 3,702,259 to Nielsen describes the use of an aqueous silver salt impregnating solution consisting essentially of a silver salt of carboxylic acid, an organic amine solubilizing/reducing agent such as ethylenediamine, a mixture of ethylenediamine or ethanolamine and ammonia or a mixture of ethylenediamine and ethanolamine. Van Bylandtlaan, in Belgium Pat. No. 808,278 (1974) employs an aqueous solution of hexamethylenetetramine with an ethylendiamine silver complex to deposit silver on an alumina support by decomposition. Additionally, it has been disclosed in Japanese Pat. No. 71/19,606 to Fujii et al that impregnation of inorganic supports with aqueous silver nitrate/alkanolamine complexes with subsequent thermal decompsition gives supported silver catalysts for ethylene epoxidation.

Recently it has been disclosed in British Pat. No. 1,413,251 to Nielsen and La Rochelle that certain alkali metals such as cesium and rubidium can be deposited on a refractory support coincidentally with the silver metal (U.S. Pat. No. 4,012,425) to form highly efficient oxide catalysts. Cesium-modified catalysts are also disclosed in U.S. Pat. No. 4,097,414 to Cavitt.

Despite the advances made in the art with regard to silver catalysts for the production of ethylene oxide there is a definite need for catalysts which exhibit an even higher oxidation selectivity to ethylene oxide.

SUMMARY OF THE INVENTION

In one aspect this invention relates to a process for making a highly-active silver catalyst which comprises:

contacting a porous, inorganic, catalyst support material with an impregnating solution; and, heating the impregnated support material at temperatures from about 50° C. to 300° C. to evaporate volatiles and activate said catalyst, wherein the said impregnating solution comprises:
 (a) a silver salt,
 (b) an organic amine solubilizing/reducing agent,
 (c) a salt of a higher alkali metal selected from the group consisting of cesium and rubidium sufficient to deposit on the said support an effective amount of the said higher alkali metal and
 (d) an aqueous solvent, and subsequently abrading the surface of the catalyst to remove about 1 to about 10 weight percent of the catalyst (Type I Catalyst).

In another aspect this invention relates to a process which comprises:

contacting a porous, inorganic catalyst support with an aqueous impregnating solution of a salt of a higher alkali metal selected from the group consisting of cesium, rubidium, and mixtures thereof sufficient to deposit on the said support an effective amount of the said higher alkali metal, drying the impregnated support at a temperature of about 50° to about 150° C., contacting the impregnated catalyst support with a second impregnating solution and heating the thus-impregnated support at a temperature of about 50° to about 300° C. to evaporate volatiles and to activate the catalyst, wherein the said second impregnating solution comprises:
 (a) silver salt,
 (b) an organic amine solubilizing/reducing agent, and
 (c) an aqueous solvent, and subsequently abrading the surface of the catalyst to remove about 1 to about 10 weight percent of the catalyst (Type II Catalyst).

Surprisingly, it has been found that the selectivity and the activity of the silver catalysts useful in the production of ethylene oxide can be improved by mechanically removing the outer surface or skin of the catalyst after the impregnated catalyst support has been heated at temperatures of about 50° to about 300° C. to evaporate the volatiles, to reduce the silver salt to silver metal and activate the catalyst. The reason for this increased activity after removal of the outer surface following the activation of the catalyst during the heating step is not fully understood. Removal of the outer surface of the catalyst can be carried out by any one of a number of methods well known in the art such as by tube milling, ball milling, tumbling, sand blasting, etc. or by any other convenient method for abrading or wearing away the outer surface of the catalyst. The weight of the catalyst removed during this final activation operation is small and generally will be as previously pointed out from about 1 to about 10 weight percent and, preferably, from about 2 to about 6 weight percent based on the initial catalyst weight.

DETAILED DESCRIPTION OF THE INVENTION

In a first step of making catalysts where the impregnating solution contains both the silver salt and the salt of cesium or rubidium (Type I Catalyst), there is prepared a solution comprising:
(a) a silver compound,
(b) an organic amine solubilizing/reducing agent,
(c) a salt of at least one higher alkali metal selected from the group consisting of cesium and rubidium and mixtures thereof sufficient to deposit on the said support an effective amount of the said higher alkali metal, and
(d) an aqueous solvent.

When the said salt of the higher alkali metal employed is cesium perchlorate, rubidium perchlorate or a mixture thereof, then the impregnating solution may also contain, if desired, a perhalogenated acid selected from the group consisting of perchloric acid, perbromic acid and periodic acid in an amount of from 0 to about 20 and preferably about 0.5 to about 8 milliequivalent weights per milliequivalent weight of the perchlorate salt in the said solution. Such an impregnating solution is formed, for example, by slurrying the silver compound such as a silver oxalate in water followed by the addition of the organic amine solubilizing/reducing agent in an amount sufficient to dissolve the silver carboxylate. Finally, to the formed aqueous solution there is added a solution of, for example, cesium hydroxide or a solution of cesium or rubidium perchlorate together with a perhalogenated acid, if desired, dissolved in an aqueous solvent which is preferably water.

In a second step, an inorganic porous support, as more fully described hereinafter, the high-purity α-alumina support, is impregnated by immersing the support in the impregnating solution at about atmospheric pressure and then subjecting the immersed support to vacuum at temperatures of from about 20° C. to about 40° C. After the vacuum is broken, the excess solution is drained. If desired, the vacuum impregnation step may be repeated. In the next step, the drained support is heated to evaporate volatiles at temperatures of from about 50° C. to 180° C. in a forced-air heater for a time from about 1 to about 12 hours. Then the dried, impregnated support is heated in the presence of forced air at temperatures of from about 180° C. to about 300° C. to decompose the silver compound and activate the supported, promoted silver catalyst material.

In a final step the thus-prepared silver catalyst is subjected to an abrading step for the purpose of removing or wearing away the surface thereof in an amount of from about 1 to about 10 weight percent of the catalyst. The thus-formed catalyst exhibits a higher selectivity in the conversion of ethylene to ethylene oxide in the presence of molecular oxygen and, in addition, the activity of the catalyst is increased.

The method of forming the catalysts of this invention where a two-step impregnation is employed (i.e., Type II Catalysts) is quite similar to the catalyst preparation method described above except that the support is first impregnated with an aqueous solution of a salt of a higher alkali metal and following a drying step the catalyst is impregnated with a solution of a silver salt, an organic amine solublizing/reducing agent and a solvent and afterward the catalyst preparation process is completed in the same way as described in connection with the catalyst prepared where the higher alkali metal promoter and the silver salt are simultaneously deposited on the support from the impregnating solution. In preparing the Type II Catalyst the concentration of the higher alkali metal in the aqueous solution will generally be from about 10 to about 1200 ppm.

Preferably, the silver compounds utilized in preparing the impregnating solutions are the silver carboxylates which readily thermally decompose. Such compounds can be carboxylates of mono-carboxylic or poly-carboxylic acids. Preferably, the silver salt is of a mono-carboxylic or di-carboxylic acid, wherein the organic moiety contains less than about 10 carbon atoms. Those carboxylates of less than about 10 carbon atoms are preferred in order to obtain a favorable concentration of silver in the organic acid salt, and ultimately thus in the complex solution, while providing for facile thermal decomposition. It should be noted that while silver salts of organic acids containing more than about 10 carbon atoms are useful, they produce a silver amine complex which becomes increasingly difficult to decompose as the molecular weight increases and will reduce the amount of silver ultimately available for deposition on the support.

Examples of suitable silver carboxylates include silver carbonate, silver acetate, silver malonate, silver glycolate, silver oxalate, silver formate, silver citrate, silver lactate, silver pyruvate, and the like. The most preferred silver carboxylates are silver oxalate and silver acetate because of availability and solubility.

The useful amine solubilizing/reducing agents employed in the catalyst impregnating solutions of the instant invention can be generically described as:
(A) vicinal aliphatic diamines having from 2 to 4 inclusive carbon atoms as exemplified by ethylene diamine, 1,2-diaminopropane, 1,2 and 2,3-diaminobutane and 1,2-diamino-2-methylpropane;
(B) alicyclic diamines wherein at least one amino moiety is primary or secondary provided no more than one amino moiety is primary;
(C) polyamines containing at least three amino moieties wherein at least one is primary or secondary; and
(D) amino ethers containing at least one ether (oxy) linkage wherein at least one amino moiety is primary or secondary.

Although all alicyclic diamines meeting the above criteria are useful as complexing agents, a preferred group of such diamines comprises piperazine, the N-alkyl substituted piperazines and the C-alkyl substituted piperazines.

While all aliphatic polyamines containing at least three amino moieties wherein at least one is primary are useful as complexing agents, a preferred group is the polyalkylene polyamines of the formula:

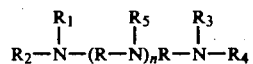

wherein R is a straight or branched chain alkylene radical having from 2 to about 4 carbon atoms, $R_1$, $R_2$, $R_3$, $R_4$ and $R_5$ are, independently, hydrogen or an alkyl radical of from 1 to 5 carbon atoms provided at least one of $R_1$, $R_2$, $R_3$, $R_4$ or $R_5$ is hydrogen; or $R_1$ and $R_2$ or $R_3$ and $R_4$ with the nitrogen to which they are attached to form a piperazine ring and n is an integer of from 1 to about 4. Examples include N(aminoethyl)-piperazine, N,N'-bis(2-aminoethyl)-piperazine, diethylenetriamine, N-methyldiethylenetriamine, triethylenetetramine, and the like. The most preferred polyalkylene polyamine compounds are diethylenetriamine and triethylenetetramine.

The amino ethers that are useful within the scope of the instant invention are the saturated and unsaturated, substituted and unsubstituted aliphatic amino ethers. These compounds may be straight or branched chain, acyclic, alicyclic, heterocyclic, or cyclic. Examples of such compounds include morpholine, the C-substituted morpholines, etc.; the bis(aminoalkyl) ethers, the N-alkyl bis(aminoalkyl) ethers, etc.; the polyoxyalkylene amines; the polyoxyalkylene polyamines, etc.; the alkoxyalkyl amines; amino-containing ethers derived from furan; and the like.

One preferred class of amino ethers is morpholine and the C-alkyl substituted morpholines. Another preferred class is the polyoxyalkyleneamines of molecular weight less than 1,000 and more preferably less than 500. Examples include the polyoxypropylenediamines of molecular weight less than about 400, and polyoxypropylenetriamine of molecular weight about 400. Both of the above polyoxypropyleneamine compounds contain terminal primary amino groups.

The amount of a particular amine utilized in preparing the silver impregnating solution is somewhat empirical. Generally that amount of amine solubilizing/reducing agent sufficient to completely dissolve the silver salts, i.e., a solubilizing amount, is utilized. This amount can be readily determined by the skilled artisan since the amount usually employed is sufficient to completely dissolve the required amount of silver salt can be determined by observation. An excess of the amine over that required to completely dissolve the silver salt can be employed, if desired. The amount of silver salt required is somewhat empirical and generally determined by the amount of silver ion required in solution and the porosity of the support.

As hereinbefore mentioned, it is desirable to have the impregnating solution as "rich" as possible in silver. Generally, the silver impregnating solution should contain an amount of about twice that desired in the finished catalyst on a weight percent basis with a support having a 50 percent porosity. It is preferably, therefore to utilize an impregnating solution which contains more than about 10 weight percent silver and, more preferably, from about 12 to about 25 weight percent silver.

When the polyalkylene polyamines, for example, are utilized, it is desirable to have from about 1 to about 6 amine equivalents of the polyalkylene polyamine for each equivalent of silver in the impregnating solution.

The silver salt is preferably solubilized in the amine-containing agent at temperatures in the range of about 20° C. to about 40° C. Temperatures in excess of 50° C. are not preferred, since high temperatures tend to cause accelerated decomposition of the complex.

Aqueous solvents useful in preparing the silver impregnating solutions of this invention include water, aqueous ammonia, and the like. In accordance with a preferred embodiment, water is utilized as the solvent. Water not only reduces the viscosity of the impregnating solution, reduces the amount of amine required to solubilize the silver salt, and reduces potential hazards of handling the solution, but also acts as an excellent solvent for the silver salt/amine complex formed by reaction of the silver salt and the amine, as well as the cesium or rubidium salt thus preventing premature precipitation.

The cesium and rubidium salts which can be utilized in preparing the silver impregnating solution include those which are soluble in an aqueous solution of the silver salt and the organic amine solubilizing/reducing agent. Since the metal is deposited on the surface of the support in the form of the cation rather than the free alkali metal, no particular effectiveness is observed with the use of any specific anion. For example, nitrates, nitrites, hydroxide, chlorides, chlorates, perchlorates, carbonates, bicarbonates, oxalates, acetates, tartrates, lactates, and the like may be used. It should be noted, however, that those cesium or rubidium salts which react with or cause the silver present in the solution to precipitate prematurely should be avoided. A cesium or rubidium salt of an organic carboxylic acid or cesium hydroxide is conveniently used. Cesium hydroxide or cesium perchlorate and the corresponding rubidium compounds are preferred.

The amount of the cesium or rubidium salt present in the impregnating solution will depend upon that amount desired in the activated catalyst, the solubility of the salt, the porosity of the support, etc. Generally that amount of the higher alkali metal sufficient to deposit from about $4 \times 10^{-5}$ gew to about $3 \times 10^{-3}$ gew of the higher alkali metal per kilogram of finished catalyst is effective. Suitable impregnating solutions for the Type I catalysts contain from about 10 ppm to about 800 ppm cesium or rubidium cation. The amount of cesium or rubidium cation required in solution is capable of determination by conventional analysis of the amount of material actually deposited. Generally, the impregnating solution should contain an amount about twice that desired in the finished catalyst on a ppm basis with a support having about 50 percent porosity.

THE SUPPORT

The support utilized to form the novel promoted silver catalyst of the instant invention can be generally described as a porous, inorganic substrate having those characteristics which are well known in the art and particularly known in the ethylene epoxidation art. Suitable supports which can be used in accordance with the instant invention are glass, alumina, silica, silica-alumina, inert metals, silicon carbide and zirconia. It is essential that the support chosen have a high porosity (i.e., high solvent absorption), low surface area and a controlled pore size. Preferably, from about 70 percent to 100 percent of the pore diameters are between about 1 and $30\mu$ and more preferably between about 1 and about $10\mu$. The advantages of the instant catalyst are particularly evident when $\alpha$-alumina supports are utilized.

A preferred support media has an average pore diameter of from about 4 to about $6\mu$ with a pore volume of from about 0.3 to about 0.6 cc/g and has a surface area less than about 1 m$^2$/g. A particularly preferred support is high purity $\alpha$-alumina having the above characteristics.

The invention will be further illustrated by the following specific examples, which are given by way of illustration and not as limitations on the scope of this invention.

EXAMPLE I

This example illustrates preparation of the stable, supported silver catalyst of the instant invention. In a first step, silver oxalate was prepared. To a beaker equipped with a magnetic stirring bar there was added 230 g of ammonium oxalate and 1500 ml of deionized water following which the beaker contents were heated to about 60° C. with stirring. A solution of 522 g of silver nitrate in 1500 ml of deionized water was prepared with mixing at 60° C. in a beaker. The silver nitrate solution was then added slowly to the ammonium oxalate solution with stirring and the resulting slurry was stirred for an additional 15 minutes while cooling in air. In the next step the slurry was filtered through a Buchner funnel after which the precipitate, i.e., the silver oxalate, was washed first with 500 ml of hot, deionized water in small increments and then with 500 ml of cold, anhydrous methanol in small aliquots. Following the removal of most of the liquid from the precipitate with vacuum suction, the moist cake was broken up and added slowly to 538 g of deionized water with stirring. The creamy, homogeneous slurry thus-obtained was cooled to below room temperature with an ice bath while 461 g of diethylenetriamine was added with stirring while keeping the solution temperature at 40° C. or below. After all solids had dissolved, sufficient deionized water was added to give a total of 1600 g of the silver solution.

A promoter solution containing cesium perchlorate and free perchloric acid was prepared by dissolving 5.28 g of 50 percent cesium hydroxide solution and 28.8 g of perchloric acid (from 15 g of 71 percent perchloric acid in 3270 g of deionized water). The promoter solution contained 4.09 g of cesium perchlorate (17.6 milliequivalents) and 1.84 g of free perchloric acid (18.3 milliequivalents).

The above-described promoter solution was utilized to impregnate a total of 2,517 g of a commercial alumina support (9/32" spherical pellets) having a pore volume of 0.469 cc/g, a surface area of less than 1 m²/g and an average pore diameter of about $7\mu$ sold under the tradename the Norton Company's "Alundum", type LSA-05588. The support, after being impregnated with the promoter solution was drained and then dried for 2 hours at 125° C. in a forced air oven with 50 percent air circulation. In the next step the promoter-impregnated support was impregnated with the above-described silver solution. During this impregnation step the support and silver solution in which the support was immersed were placed under vacuum and then the vacuum was released after which the wet catalyst was drained, spread on three 14" by 16" trays and placed in a forced-air production oven preheated to 150° C. With the damper set at 25 percent air recirculation the catalyst was heated for 2 hours at 125°-130° C. Then the temperature was increased to 250° C. and maintained at that temperature for 1 hour with maximum air intake with exhaust 75 percent closed. The thus-treated catalyst was cooled to 50° C., then bottled and weighed. A total of 2,576 g of silver-gray catalyst was recovered. A sample of this catalyst (Catalyst AA) was submitted for silver and cesium analyses by atomic absorption.

Catalyst AA was tested in a minature ethylene oxide reactor employing 3.5 g of whole pellets in a ⅜ inch stainless steel reactor tube. The test was run at reactor temperature of 235, a gas flow rate of about 130 standard cubic centimeters per minute and a reactor pressure of 200 psig. The feed gas composition was 30 mole percent ethylene (99.8 minimum mole percent purity), 8 mole percent oxygen, 30 mole percent methane and the balance nitrogen. The ethylene dichloride inhibitor concentration in the feed was about 3-4 ppm.

A large bulk sample of Catalyst AA (about 5.5 lbs) was then abraded for 5 min. in a rotating 5 gallon pail having four lifters (i.e., ridges) and lined with No. 100 sandpaper. The catalyst was tumbled at the rate of 1 rev/sec. A sample of this once-ground catalyst (Catalyst BB) was submitted for silver and cesium analysis and the catalyst was tested as before in the miniature reactor. It was determined by weighing that 3 weight percent of the catalyst has been removed during the abrading operation.

The large bulk sample was returned to the drum and abraded again in the same manner for 5 minutes. This reground catalyst (Catalyst CC) was tested as before in the miniature reactor.

Test data for Catalysts AA, BB and CC are set out in Table 1. At comparable reactor temperatures, the data indicate that the increase in ethylene oxide production (i.e., $\Delta$EO) achieved with Catalyst BB over Catalyst AA is about 28 percent and that with the tests conducted at the same ethylene oxide production rate the selectivity ($S_3$) is about 2 percent greater than that achieved with Catalyst AA at an 8° C. lower operating temperature.

TABLE 1

| Catalyst | AA | BB | CC |
|---|---|---|---|
| Total surface removed, wt % | none | 3 | 6 |
| Ag, wt % on catalyst | 11.3 | 10.7 | 10.7 |
| Cs, ppm on catalyst | 319* | 215* | 247 |
| Reactor Temperature | 235° C. | 235° C. | 237° C. |
| $\Delta$EO, mol %[1] | 1.79 | 2.55 | 2.51 |
| $S_3$, mol %[2] | 81.9 | 81.7 | 82.6 |
| $\Delta$EO, mol %[1] | 1.79 mol % | 1.79 mol % | 1.89 mol % |
| Temp, °C. | 235 | 227 | 227 |
| $S_3$, mol %[2] | 81.9 | 83.7 | 83.9 |

*Analyses not repeatable - Cs concentration on surface of pellets not uniform from pellet to pellet.
[1] Ethylene oxide in reactor exit stream.
[2] Selectivity to ethylene oxide based on oxygen converted.

What is claimed is:

1. A process for making a highly-active silver catalyst for the vapor phase epoxidation of ethylene with an oxygen-containing gas which comprises:
   contacting a porous, inorganic, catalyst support material with an impregnating solution; and,
   heating the impregnated support material at temperatures from about 50° C. to 300° C. to evaporate volatiles and activate said catlyst,
   wherein the said impregnating solution comprises:
   (a) a silver salt,
   (b) an organic amine solubilizing/reducing agent,
   (c) a salt of a higher alkali metal selected from the group consisting of cesium and rubidium sufficient to deposit on the said support an effective amount of the said higher alkali metal, and
   (d) an aqueous solvent and subsequently abrading the surface of the catalyst to remove about 1 to about 10 weight percent of the catalyst.

2. The process of claim 1 wherein the said organic amine solubilizing/reducing agent is selected from the group consisting of:
   (A) vicinal alkylenediamines of from 2 to 4 inclusive carbon atoms,
   (B) alicyclic diamines wherein at least one amino moiety is primary or secondary provided no more than one amino moiety is primary;
   (C) aliphatic polyamines containing at least three amino moieties wherein at least one is primary or secondary; and
   (D) aliphatic amino ethers containing at least one ether linkage and at least one amino moiety which is primary or secondary.

3. The process of claim 1 wherein the said organic amine is an aliphatic polyamine containing at least three amino moieties wherein at least one is primary or secondary.

4. The process of claim 1 wherein the said organic amine is diethylenetriamine.

5. The process of claim 1 wherein the impregnating solution contains from about 12 to about 25 weight percent of silver.

6. The process of claim 1 wherein the silver salt in the said impregnating solution is a silver salt of an organic acid selected from the group consisting of mono-carboxylic acids, dicarboxylic acids and mixtures thereof and wherein the organic moiety in the said acids contains less than 10 atoms.

7. The process of claim 1 wherein the silver salt in the said impregnating solution is selected from the group consisting of silver carbonate, silver acetate, silver malonate, silver glycolate, silver oxalate, silver formate, silver citrate, silver lactate and silver pyruvate.

8. The process of claim 1 wherein in the said impregnating solution the solvent is water.

9. The process of claim 1 wherein in (c) the said salt is selected from the group consisting of cesium perchlorate, rubidium perchlorate and mixtures thereof and wherein the said impregnating solution also contains a perhalogenated acid selected from the group consisting of perchloric acid, periodic acid, perbromic acid and mixtures thereof in an amount of from 0 to 20 milliequivalent weights per milliequivalent weight of the perchlorate salt in the said solution.

10. The process of claim 1 wherein the said salt of the higher alkali metal is in the impregnating solution is cesium perchlorate.

11. The process of claim 1 wherein the said salt of the higher alkali metal in the impregnating solution is rubidium perchlorate.

12. The process of claim 9 wherein the said salt is cesium perchlorate and the impregnating solution contains from about 0.5 to about 8 milliequivalent weights of the perhalogenated acid per milliequivalent weight of the perchlorate salt.

13. The process of claim 9 wherein the said salt is rubidium perchlorate and the impregnating solution contains about 0.5 to about 8 milliequivalent weights of perchloric acid per milliequivalent weight of rubidium perchlorate.

14. A process for making a highly-active silver catalyst for the vapor phase phase epoxidation of ethylene with an oxygen-containing gas which comprises:
contacting a porous, inorganic catalyst support with an aqueous impregnating solution of a salt of a higher alkali metal selected from the group consisting of cesium, rubidium, and mixtures thereof sufficient to deposit on the said support an effective amount of the said higher alkali metal,
drying the impregnated support at a temperature of about 50° to about 150° C.
contacting the impregnated catalyst support with a second impregnating solution and heating the thus-impregnated support at a temperature of about 50° to about 300° C. to evaporate volatiles and to activate the catalyst,
wherein the second impregnating solution comprises:
(a) silver salt,
(b) an organic amine solubilizing/reducing agent, and
(c) an aqueous solvent, and subsequently abrading the surface of the catalyst to remove about 1 to about 10 weight percent of the catalyst.

15. The process of claim 14 wherein the said organic amine solubilizing/reducing agent is selected from the group consisting of:
(A) vicinal alkylenediamines of from about 2 to 4 inclusive carbon atmos,
(B) alicyclic diamines wherein at least one amino moiety is primary or secondary provided no more than one amino moiety is primary;
(C) aliphatic polyamines containing at least three amino moieties wherein at least one is primary or secondary; and
(D) aliphatic amino ethers containing at least one ether linkage and at least one amino moiety which is primary or secondary.

16. The process of claim 14 wherein the said organic amine is an aliphatic polyamine containing at least three amino moieties wherein at least one is primary or secondary.

17. The process of claim 14 wherein the said organic amine is diethylenetriamine.

18. The process of claim 14 wherein the said second impregnating solution contains from about 12 to about 25 weight percent of silver.

19. The process of claim 14 wherein the silver salt is a silver salt of an organic acid selected from the group consisting of monocarboxylic acids, dicarboxylic acids and mixtures thereof and wherein the organic moiety in the said acids contains less than 10 carbon atoms.

20. The process of claim 14 wherein the silver salt is selected from the group consisting of silver carbonate, silver acetate, silver malonate, silver glycolate, silver oxalate, silver formate, silver citrate, silver lactate and silver pyruvate.

21. The process of claim 14 wherein in the said second impregnating solution the solvent is water.

22. The process of claim 14 wherein the said salt of the higher alkali metal is cesium perchlorate.

23. The process of claim 14 wherein the said salt of the higher alkali metal in the impregnating solution is rubidium perchlorate.

24. The process of claim 14 wherein the said higher alkali metal salt is selected from the group consisting of cesium perchlorate, rubidium perchlorate and mixtures thereof and wherein the said impregnating solution also contains a perhalogenated acid selected from the group consisting of perchloric acid, periodic acid, perbromic acid and mixtures thereof in an amount of from 0 to 20 milliequivalent weights per milliequivalent weight of the perchlorate salt in the said solution.

25. The process of claim 24 wherein the said salt is cesium perchlorate and the impregnating solution contains from about 0.5 to about 8 milliequivalent weights of the perhalogenated acid per milliequivalent weight of the perchlorate salt.

26. The process of claim 24 wherein the said salt is rubidium perchlorate and the impregnating solution contains about 0.5 to about 8 milliequivalent weights of perchloric acid per milliequivalent weight of rubidium perchlorate.

* * * * *